United States Patent
Hilgren et al.

(10) Patent No.: US 9,247,738 B2
(45) Date of Patent: *Feb. 2, 2016

(54) METHOD AND COMPOSITION FOR INHIBITION OF MICROBIAL GROWTH IN AQUEOUS FOOD TRANSPORT AND PROCESS STREAMS

(75) Inventors: John D. Hilgren, Shoreview, MN (US); Francis L. Richter, Hugo, MN (US); Joy A. Salverda, Woodbury, MN (US); Heidi M. Hanson, Minneapolis, MN (US); Paul F. Schacht, Oakdale, MN (US); Timothy A. Gutzmann, Eagan, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/352,971

(22) Filed: Jan. 18, 2012

(65) Prior Publication Data

US 2013/0017301 A1 Jan. 17, 2013

Related U.S. Application Data

(62) Division of application No. 11/635,145, filed on Dec. 6, 2006, now Pat. No. 8,124,132, which is a division of application No. 09/614,631, filed on Jul. 12, 2000, now Pat. No. 7,150,884.

(51) Int. Cl.
*A01N 37/02* (2006.01)
*A01N 37/16* (2006.01)
*A01N 59/00* (2006.01)

(52) U.S. Cl.
CPC .............. *A01N 37/02* (2013.01); *A01N 37/16* (2013.01); *Y10S 424/06* (2013.01)

(58) Field of Classification Search
CPC ........ A01N 37/02; A01N 37/16; A01N 59/00
USPC ........... 424/616; 514/557, 558, 560; 426/331, 426/335
See application file for complete search history.

(56) References Cited

U.S. PATENT DOCUMENTS

| | | |
|---|---|---|
| 2,512,640 A | 6/1950 | Greenspan et al. |
| 3,122,417 A | 2/1964 | Blaser et al. |
| 3,248,281 A | 4/1966 | Goodenough |
| 3,350,265 A | 10/1967 | Rubinstein et al. |
| 3,514,278 A | 5/1970 | Brink |
| 3,895,116 A | 7/1975 | Herting et al. |
| 3,996,386 A | 12/1976 | Malkki et al. |
| 4,041,149 A | 8/1977 | Gaffar et al. |
| 4,051,058 A | 9/1977 | Böwing et al. |
| 4,051,059 A | 9/1977 | Böwing et al. |
| 4,129,517 A | 12/1978 | Eggensperger et al. |
| 4,191,660 A | 3/1980 | Schreiber et al. |
| 4,244,884 A | 1/1981 | Hutchins et al. |
| 4,289,728 A | 9/1981 | Peel et al. |
| 4,370,199 A | 1/1983 | Orndorff |
| 4,404,040 A | 9/1983 | Wang |
| 4,477,438 A | 10/1984 | Willcockson et al. |
| 4,478,683 A | 10/1984 | Orndorff |
| 4,501,681 A | 2/1985 | Groult et al. |
| 4,529,534 A | 7/1985 | Richardson |
| 4,557,898 A | 12/1985 | Greene et al. |
| 4,566,980 A | 1/1986 | Smith |
| 4,591,565 A | 5/1986 | Branner-Jorgensen et al. |
| 4,592,488 A | 6/1986 | Simon et al. |
| 4,613,452 A | 9/1986 | Sanderson |
| 4,655,781 A | 4/1987 | Hsieh et al. |
| 4,659,494 A | 4/1987 | Soldanski et al. |
| 4,666,622 A | 5/1987 | Martin et al. |
| 4,683,618 A | 8/1987 | O'Brien |
| 4,704,404 A | 11/1987 | Sanderson |
| 4,715,980 A | 12/1987 | Lopes et al. |
| 4,738,840 A | 4/1988 | Simon et al. |
| 4,802,994 A | 2/1989 | Mouché et al. |
| 4,834,900 A | 5/1989 | Soldanski et al. |
| 4,865,752 A | 9/1989 | Jacobs |
| 4,900,721 A | 2/1990 | Bansemir et al. |
| 4,906,617 A | 3/1990 | Jacquet et al. |
| 4,908,306 A | 3/1990 | Lorincz |
| 4,917,815 A | 4/1990 | Beilfuss et al. |
| 4,923,677 A | 5/1990 | Simon et al. |
| 4,937,066 A | 6/1990 | Vlock |
| 4,943,414 A | 7/1990 | Jacobs et al. |

(Continued)

FOREIGN PATENT DOCUMENTS

| | | |
|---|---|---|
| CA | 2181416 | 1/1997 |
| DE | 30 03 875 A1 | 8/1981 |

(Continued)

OTHER PUBLICATIONS

FSTA abstract 2000(06):J1220; abstracting, Park, C.M. et al., "Evaluation of sanitizers for killing Escherichia coli O157:H7 . . . " Dairy, Food and Environmental Sanitation, 19(12), pp. 842-847 (Dec. 1999).*

Taylor, J.H. et al., "A comparison of the bactericidal efficacy of 18 disinfectants used in the food industry against Escherichia coli O157:H7 . . . " Journal of Applied Microbiology, vol. 87, pp. 718-725 (1999).*

"Emery® Fatty and Dibasic Acids Specifications and Characteristics", *Emery Industries*, Bulletin 145 (Oct. 1983).

(Continued)

*Primary Examiner* — John Pak
(74) *Attorney, Agent, or Firm* — Merchant & Gould P.C.

(57) ABSTRACT

The present invention relates to compositions including peroxyacetic acid and peroxyoctanoic acid and methods for preventing microbial growth in aqueous streams including the step of applying a composition of the invention to the stream. The compositions and methods can control microbial growth in aqueous streams used for transporting or processing food products.

7 Claims, 2 Drawing Sheets

(56) References Cited

U.S. PATENT DOCUMENTS

| | | | |
|---|---|---|---|
| 4,945,110 A | 7/1990 | Brokken et al. | |
| 4,996,062 A | 2/1991 | Lehtonen et al. | |
| 4,997,571 A | 3/1991 | Roensch et al. | |
| 4,997,625 A | 3/1991 | Simon et al. | |
| 5,004,760 A | 4/1991 | Patton et al. | |
| 5,010,109 A | 4/1991 | Inoi | |
| 5,015,408 A | 5/1991 | Reuss | |
| 5,043,176 A | 8/1991 | Bycroft et al. | |
| 5,069,286 A | 12/1991 | Roensch et al. | |
| 5,078,896 A | 1/1992 | Rorig et al. | |
| 5,084,239 A | 1/1992 | Moulton et al. | |
| 5,093,140 A | 3/1992 | Watanabe | |
| 5,114,178 A | 5/1992 | Baxter | |
| 5,114,718 A | 5/1992 | Damani | |
| 5,122,538 A | 6/1992 | Lokkesmoe et al. | |
| 5,129,824 A | 7/1992 | Keller | |
| 5,130,124 A | 7/1992 | Merianos et al. | |
| 5,139,788 A | 8/1992 | Schmidt | |
| 5,176,899 A | 1/1993 | Montgomery | |
| 5,184,471 A | 2/1993 | Losacco et al. | |
| 5,200,189 A | 4/1993 | Oakes et al. | |
| 5,208,057 A | 5/1993 | Greenley et al. | |
| 5,234,703 A | 8/1993 | Guthery | |
| 5,234,719 A | 8/1993 | Richter et al. | |
| 5,266,587 A | 11/1993 | Sankey et al. | |
| 5,268,003 A | 12/1993 | Coope et al. | |
| 5,292,447 A | 3/1994 | Venturello et al. | |
| 5,314,687 A | 5/1994 | Oakes et al. | |
| 5,320,805 A | 6/1994 | Kramer et al. | |
| 5,336,500 A | 8/1994 | Richter et al. | |
| 5,364,650 A | 11/1994 | Guthery | |
| 5,391,324 A | 2/1995 | Reinhardt et al. | |
| 5,409,713 A | 4/1995 | Lokkesmoe et al. | |
| 5,419,908 A | 5/1995 | Richter et al. | |
| 5,435,808 A | 7/1995 | Holzhauer et al. | |
| 5,436,008 A | 7/1995 | Richter et al. | |
| 5,437,868 A | 8/1995 | Oakes et al. | |
| 5,489,434 A | 2/1996 | Oakes et al. | |
| 5,489,706 A | 2/1996 | Revell | |
| 5,494,588 A | 2/1996 | LaZonby | |
| 5,508,046 A | 4/1996 | Cosentino et al. | |
| 5,512,309 A | 4/1996 | Bender et al. | |
| 5,527,898 A | 6/1996 | Bauer et al. | |
| 5,545,343 A | 8/1996 | Brougham et al. | |
| 5,545,374 A | 8/1996 | French et al. | |
| 5,578,134 A | 11/1996 | Lentsch et al. | |
| 5,591,706 A | 1/1997 | Ploumen | |
| 5,595,967 A | 1/1997 | Miracle et al. | |
| 5,597,790 A | 1/1997 | Thoen | |
| 5,616,335 A | 4/1997 | Nicolle et al. | |
| 5,616,616 A | 4/1997 | Hall et al. | |
| 5,624,634 A | 4/1997 | Brougham et al. | |
| 5,632,676 A | 5/1997 | Kurschner et al. | |
| 5,641,530 A | 6/1997 | Chen | |
| 5,656,302 A | 8/1997 | Cosentino et al. | |
| 5,658,467 A | 8/1997 | LaZonby et al. | |
| 5,674,538 A * | 10/1997 | Lokkesmoe et al. | 424/616 |
| 5,674,828 A | 10/1997 | Knowlton et al. | |
| 5,683,724 A | 11/1997 | Hei et al. | |
| 5,692,392 A | 12/1997 | Swier | |
| 5,712,239 A | 1/1998 | Knowlton et al. | |
| 5,718,910 A * | 2/1998 | Oakes et al. | 424/405 |
| 5,720,983 A | 2/1998 | Malone | |
| 5,756,139 A | 5/1998 | Harvey et al. | |
| 5,785,867 A | 7/1998 | LaZonby et al. | |
| 5,840,343 A | 11/1998 | Hall et al. | |
| 5,851,483 A | 12/1998 | Nicolle et al. | |
| 5,891,392 A | 4/1999 | Monticello et al. | |
| 5,900,256 A | 5/1999 | Scoville, Jr. et al. | |
| 5,902,619 A | 5/1999 | Rubow et al. | |
| 5,968,539 A | 10/1999 | Beerse et al. | |
| 5,989,611 A | 11/1999 | Stemmler, Jr. et al. | |
| 5,998,358 A | 12/1999 | Herdt et al. | |
| 6,008,405 A | 12/1999 | Gray et al. | |
| 6,010,729 A | 1/2000 | Gutzmann et al. | |
| 6,024,986 A | 2/2000 | Hei | |
| 6,028,104 A | 2/2000 | Schmidt et al. | |
| 6,033,705 A | 3/2000 | Isaacs | |
| 6,039,992 A | 3/2000 | Compadre et al. | |
| 6,049,002 A | 4/2000 | Mattila et al. | |
| 6,080,712 A | 6/2000 | Revell et al. | |
| 6,096,226 A | 8/2000 | Fuchs et al. | |
| 6,096,266 A | 8/2000 | Duroselle | |
| 6,096,348 A | 8/2000 | Miner et al. | |
| 6,165,483 A * | 12/2000 | Hei et al. | 424/405 |
| 6,238,685 B1 * | 5/2001 | Hei et al. | 424/405 |
| 6,257,253 B1 | 7/2001 | Lentsch et al. | |
| 6,274,542 B1 | 8/2001 | Carr et al. | |
| 6,302,968 B1 | 10/2001 | Baum et al. | |
| 6,326,032 B1 | 12/2001 | Richter et al. | |
| 6,395,703 B2 | 5/2002 | Scepanski | |
| 6,451,746 B1 | 9/2002 | Moore et al. | |
| 6,514,556 B2 * | 2/2003 | Hilgren et al. | 426/652 |
| 6,545,047 B2 | 4/2003 | Gutzmann et al. | |
| 6,630,439 B1 | 10/2003 | Norwood et al. | |
| 6,635,286 B2 | 10/2003 | Hei et al. | |
| 6,638,902 B2 | 10/2003 | Tarara et al. | |
| 7,150,884 B1 | 12/2006 | Hilgren et al. | |
| 7,381,439 B2 * | 6/2008 | Hilgren et al. | 426/321 |
| 2002/0128312 A1 | 9/2002 | Hei et al. | |
| 2003/0087786 A1 | 5/2003 | Hei et al. | |
| 2003/0199583 A1 | 10/2003 | Gutzmann et al. | |

FOREIGN PATENT DOCUMENTS

| | | |
|---|---|---|
| DE | 35 43 500 A1 | 6/1987 |
| DE | 39 06 044 A1 | 8/1990 |
| DE | 197 51 391 A1 | 7/1998 |
| DK | 0538/9310 | 5/1993 |
| EP | 0 186 052 A1 | 7/1986 |
| EP | 0 195 619 A2 | 9/1986 |
| EP | 0 125 781 B1 | 8/1987 |
| EP | 0 233 731 A2 | 8/1987 |
| EP | 0 242 990 A2 | 10/1987 |
| EP | 0 140 648 B1 | 3/1989 |
| EP | 0 361 955 A2 | 4/1990 |
| EP | 0 404 293 A2 | 12/1990 |
| EP | 0 461 700 A1 | 12/1991 |
| EP | 0 569 066 A1 | 11/1993 |
| EP | 0 667 392 A2 | 8/1995 |
| EP | 0 460 962 B1 | 12/1995 |
| EP | 0 779 357 A1 | 6/1997 |
| EP | 0 603 329 B1 | 8/1997 |
| EP | 0 805 198 A1 | 11/1997 |
| EP | 0 843 001 A1 | 5/1998 |
| EP | 0 967 203 A1 | 12/1999 |
| EP | 0 985 349 A2 | 3/2000 |
| EP | 1 382 666 A1 | 1/2004 |
| FR | 2 321 301 A | 3/1977 |
| FR | 2 324 626 A | 4/1977 |
| FR | 2 578 988 A1 | 9/1986 |
| GB | 1 494 109 | 12/1977 |
| GB | 1 570 492 | 7/1980 |
| GB | 2 182 051 A | 5/1987 |
| GB | 2 187 958 | 9/1987 |
| GB | 2 207 354 A | 2/1989 |
| GB | 2 255 507 | 11/1992 |
| GB | 2 257 630 A | 1/1993 |
| GB | 2 353 800 A | 3/2001 |
| JP | 7031210 | 2/1995 |
| JP | 7258005 | 10/1995 |
| JP | 2000342237 | 12/2000 |
| LU | 78 568 A | 4/1978 |
| NL | 9201631 | 9/1992 |
| RU | 2102447 C1 | 8/1996 |
| WO | WO 93/01716 | 2/1993 |
| WO | WO 94/06294 | 3/1994 |
| WO | WO 94/14321 | 7/1994 |
| WO | WO 94/15465 | 7/1994 |
| WO | WO 94/21122 * | 9/1994 |
| WO | WO 94/23575 | 10/1994 |
| WO | WO 95/34537 | 12/1995 |
| WO | WO 96/30474 | 10/1996 |
| WO | WO 98/28267 | 7/1998 |

(56) References Cited

FOREIGN PATENT DOCUMENTS

| WO | WO 99/51095 | * 10/1999 |
|---|---|---|
| WO | WO 00/18870 | 4/2000 |
| WO | WO 01/47359 A2 | 7/2001 |

OTHER PUBLICATIONS

"Indirect food additives: adjuvants, production aids, and sanitizers", *Fed. Regist.*, vol. 61, No. 108, pp. 28051-28053 (Jun. 4, 1996) (abstract only).
Armak Chemicals, "NEO-FAT Fatty Acids", *Akzo Chemicals Inc.*, Bulletin No. 86-17 (1986).
Baldry, M.G.C., "The bactericidal, fungicidal and sporicidal properties of hydrogen peroxide and peracetic acid," *Journal of Applied Bacteriology*, vol. 54, pp. 417-423 (1983).
Baldry et al., "Disinfection of Sewage Effluent with Peracetic Acid," *Wat. Sci. Tech.*, vol. 21, No. 3, pp. 203-206 (1989).
Baldry et al., "Disinfection with peroxygens," *Industrial Biocides*, edited by K.R. Payne, New York, John Wiley & Sons, pp. 91-116.
Bayliss et al., "The Synergistic Killing of Spores of *Bacillus subtilis* by Hyrdrogen Peroxide and Ultra-Violet Light Irradiation," *FEMS Microbiology Letters*, vol. 5, pp. 331-333 (1979).
Bell, K. et al., "Reduction of foodborne micro-organisms on beef carcass tissue using acetic acid, sodium bicarbonate, and hydrogen peroxide spray washes", *Food Microbiology*, vol. 14, pp. 439-448 (1997).
Beuchat, Larry R., "Surface Disinfection of Raw Produce," *Dairy, Food and Environmental Sanitation*, vol. 12, No. 1, pp. 6-9 (Jan. 1992).
Block, Seymour S., "Peroxygen Compounds," *Disinfection, Sterilization, and Preservation*, Fourth Edition, Chapter 9, pp. 167-181 (1991).
Block, Seymour S., "Peroxygen Compounds," *Disinfection, Sterilization and Preservation*, Fifth Edition, Chapter 9, pp. 185-204 (2001).
Breen, P. et al., "Quaternary Ammonium Compounds Inhibit and Reduce the Attachment of Viable *Salmonella typhimurium* to Poultry Tissues", *Journal of Food Science*, vol. 60, No. 6, pp. 1191-1196 (1995).
Breen, P. et al., "Elimination of *Salmonella* Contamination from Poultry Tissues by Cetylpyridinium Chloride Solutions", *Journal of Food Protection*, vol. 60, No. 9, pp. 1019-1021 (1997).
Brown, G. Eldon, "Use of Xanthomonas-campestris pv-vesicatoria to Evaluate Surface Disinfectants for Canker Quarantine Treatment of Citrus Fruit," *Plant Disease*, pp. 319-323 (Apr. 1987).
Computer search results—Level 1-5 patents (Mar. 1994).
Computer search results from Ecolab Information Center (Jun. 1998).
International Search Report dated Jan. 30, 2002.
International Search Report dated Jun. 3, 2002.
International Search Report dated Dec. 27, 2002.
Cords, B.R., "New Peroxyacetic Acid Sanitizer", *Proceedings*, Twenty-Third Convention, Institute of Brewing, Sydney Australia, pp. 165-169 (1994).
Dickens, J. et al., "The Effect of Acetic Acid and Air Injection on Appearance, Moisture Pick-Up, Microbiological Quality, and *Salmonella* Incidence on Processed Poultry Carcasses", *Poultry Science*, vol. 73, pp. 582-586 (1994).
Dickens, J. et al., "The Effect of an Acetic Acid Dip on Carcass Appearance, Microbiological Quality, and Cooked Breast Meat Texture and Flavor", *Poultry Science*, vol. 73, pp. 576-581 (1994).
Dickens, J. et al., "The Effects of Extended Chilling Times with Acetic Acid on the Temperature and Microbiological Quality of Processed Poultry Carcasses", *Poultry Science*, vol. 74, pp. 1044-1048 (1995).
Dickens, J. et al., "Effects of Acetic Acid and Hydrogen Peroxide Application During Defeathering on the Microbiological Quality of Broiler Carcasses Prior to Evisceration", *Poultry Science*, vol. 76, pp. 657-660 (1997).
Dickinson, J. et al., "Microbiological Decontamination of Food Animal Carcasses by Washing and Sanitizing Systems: A Review", *Journal of Food Protection*, vol. 55, No. 2, pp. 133-140 (Feb. 1992).
Eggensperger, H., "Disinfectants Based on Peracid-Splitting Compounds", *Zbl. Bakt. Hyg*., I. Abt. Orig. B, vol. 168, pp. 517-524 (1979).
Focus on Interox, *Effluent + Water Treatment Journal* (Aug. 1979).
Fraser, J.A.L., "Novel applications of peracetic acid in industrial disinfection," *Specialty Chemicals*, vol. 7, No. 3, pp. 178, 180, 182, 184, 186 (1987).
FSTA abstract, accession No. 1999(10):C1223, abstracting: *Journal of Food Protection*, vol. 62, No. 7, pp. 761-765 (1999).
FSTA abstract, accession No. 2000(06):J1220, abstracting: *Dairy, Food and Environmental Sanitation*, vol. 19, No. 12, pp. 842-847 (1999).
Greenspan et al., "The Application of Peracetic Acid Germicidal Washes to Mold Control of Tomatoes," *Food Technology*, vol. 5, No. 3, pp. 95-97 (Mar. 1951).
Han et al., "Destruction of Bacterial Spores on Solid Surfaces," *Journal of Food Processing and Preservation*, vol. 4, No. 1-2, pp. 95-110 (1980).
Heinemann, P.G., "The Germicidal Efficiency of Commercial Preparations of Hydrogen Peroxid," *The Journal of the American Medical Association*, vol. LX, No. 21, pp. 1603-1606 (1913).
Hutchings et al., "Comparative Evaluation of the Bactericidal Efficiency of Peracetic Acid, Quaternaries, and Chlorine-Containing Compounds," *Presented at the 49th General Meeting of the Society of American Bacteriologists*, (Abstract) pp. 50-51 (1949).
Interox Chemicals Ltd. product brochure entitled: OXYMASTER Peracetic Acid 12%.
Interox Chemicals Ltd. product brochure entitled: PROXITANE 4002 Peracetic Acid 36-40%.
Jager et al., "Peracetic acid as a disinfectant in breweries and soft drink factories," *Mitt. Versuch. Gaorung. Wien*., vol. 34, pp. 32-36 (1980).
Kim, J. et al., "Cetylpyridinium Chloride (CPC) Treatment on Poultry Skin to Reduce Attached *Salmonella", Journal of Food Protection*, vol. 59, No. 3, pp. 322-326 (1995).
Kunzmann, T., "Investigations on the disinfecting action of hydrogen peroxides," *Fortschr. Med*., vol. 52, No. 16, pp. 357-359 (1934).
Laska, M. et al., "Odor structure-activity relationships of carboxylic acids correspond between squirrel monkeys and humans", *Am. J. Physiol*., vol. 274, pp. R1639-R1645 (1998).
Lillard, H., "Bacterial Cell Characteristics and Conditions Influencing their Adhesion to Poultry Skin", *Journal of Food Protection*, vol. 48, No. 9, pp. 803-807 (Sep. 1985).
Lillard, H., "Factors Affecting the Persistence of *Salmonella* During the Processing of Poultry", *Journal of Food Protection*, vol. 52, No. 11, pp. 829-832 (Nov. 1989).
Lion C. et al., "New decontaminants. Reaction of peroxyacid esters with toxic insecticides", *Bull. Soc. Chim. Belg*., vol. 100, No. 7, pp. 555-559 (1991).
Merka, V. et al., "Disinfectant properties of some peroxide compounds.", Abstract No. 67542e, *Chemical Abstracts*, vol. 67 (1967).
MicroPatent Report dated Aug. 18, 2003.
Mulder, R.W.A.W. et al., "Research Note: Salmonella Decontamination of Broiler Carcasses with Lactic Acid, L-Cysteine, and Hdrogen Peroxide", *Poultry Science*, vol. 66, pp. 1555-1557 (1987).
Nambudripad et al., "Bactericidal Efficiency of Hydrogen Peroxide Part I. Influence of different concentrations on the rate and extent of destruction of some bacteria of dairy importance," *Indian Journal of Dairy Science*, vol. 4, pp. 65-69 (Jan. 22, 1949).
Opinion Letter dated Apr. 11, 2000.
Orth et al., "Is the control of *Listeria, Campylobacter* and *Yersinia* a disinfection problem?", *Fleischwirtsch*, vol. 69, No. 10, pp. 1575-1576 (1989).
Parker, W. et al., "Peroxides. II. Preparation, Characterization and Polarographic Behavior of Longchaing Aliphatic Peracids", *Synthesis and Properties of LongChain Aliphatic Peracids*, vol. 77, pp. 4037-4041 (Aug. 1955).
Parker, W. et al., "Peroxides. IV. Aliphatic Diperacids", *Aliphatic Diperacids*, vol. 79, pp. 1929-1931 (Apr. 20, 1957).

(56) References Cited

OTHER PUBLICATIONS

Pfizer Chemical Division, "Pfizer Flocon® Biopolymers for Industrial Uses (xanthan broths)", Data Sheet 679, pp. 1-4 (year unknown).
Poffe et al., "Disinfection of Effluents from Municipal Sewage Treatment Plants with Peroxy Acids," *Zbl. Bakt. Hyg., I. Abt. Orig.* B, vol. 167, pp. 337-346 (1978).
Ranganna et al., "Chemical Preservatives and Antioxidants," *Indian Food Packer*, pp. 30-44 (May-Jun. 1981).
Richardson, B.W., "On Peroxide of Hydrogen, or Ozone Water, as a Remedy," *The Lancet*, pp. 707-709, 760-763 (Mar. 1891).
Search Report for the use of amine oxides with hydrogen peroxide in bleaching, sanitizing, disinfectant or hard surface cleaners.
Search Result from Database WPI and Database INPADOC.
Search Results (2003).
Sims, Alan F.E., "Industrial effluent treatment with hydrogen peroxide," *Chemistry and Industry*, No. 14, pp. 555-558 (1983).
Solvay product brochure entitled: Oxymaster®-Proxitane® Peracetic Acid Applications.
Solvay product brochure entitled: Oxymaster®-Proxitane® Peracetic Acid Solutions; Handling, Storage and Transport Information (Safety Documentation).
Tamblyn, K. et al., "Bactericidal Activity of Organic Acids against *Salmonella typhimurium* Attached to Broiler Chicken Skin", *Journal of Food Protection*, vol. 60, No. 6, pp. 629-633 (1997).
Taylor, J. et al., "A comparison of the bactericidal efficacy of 18 disinfectants used in the food industry against *Escherichia coli* O157:H7 and *Pseudomonas aeruginosa* at 10 and 20° C.," *Journal of Applied Microbiology*, vol. 87, pp. 718-725 (1999).
Towle, G. et al., "Industrial Gums polysaccharides and Their Derivatives", Second Edition, Ch. XIX, "Pectin", pp. 429-444 (year unknown).
Xiong, H. et al., "Spraying Chicken Skin with Selected Chemicals to Reduce Attached *Salmonella typhimurium*", *Journal of Food Protection*, vol. 61, No. 3, pp. 272-275 (1998).
Yoshpe et al., "Disinfection of Water by Hydrogen Peroxide," *Health Laboratory Science*, vol. 5, No. 4, pp. 233-238 (1968).

\* cited by examiner

METHOD AND COMPOSITION FOR INHIBITION OF MICROBIAL GROWTH IN AQUEOUS FOOD TRANSPORT AND PROCESS STREAMS

CROSS REFERENCE TO RELATED APPLICATION

This application is a divisional of U.S. patent application Ser. No. 11/635,145, filed Dec. 6, 2006 and issued as U.S. Pat. No. 8,124,132 on Feb. 28, 2012, which is a divisional of U.S. patent application Ser. No. 09/614,631, filed Jul. 12, 2000, issued as U.S. Pat. No. 7,150,884 on Dec. 19, 2006. The entire disclosures of which are hereby expressly incorporated herein by reference including, without limitation, the specification, claims, and abstracts, as well as any figures, tables, or drawings thereof.

FIELD OF THE INVENTION

The present invention relates to compositions including peroxyacetic acid and peroxyoctanoic acid and methods for preventing microbial growth in aqueous streams including the step of applying a composition of the invention to the stream. The compositions and methods can control microbial growth in aqueous streams used for transporting or processing food products.

BACKGROUND OF THE INVENTION

One method of handling a large volume of foods, such as, for example, fruits and vegetables, is after selection, to transport these various food stuffs by an aqueous medium to transport the food stuffs through various cleaning, handling, and processing steps and environments. For example, in specific applications, fresh fruits and vegetables can be transported through water streams by food handling equipment used at a processing plant. After picking, fruits and vegetables are introduced into a flume system wherein water acts as a transport medium and a cleaning medium. Water can be used to support and transport the fruits or vegetables from an unloading site to a final storage or packing or processing location. During the transport, water can take a food item from an initial location through a series of somewhat separate stages to a final station where the produce is removed from the water and packed. The water within each stage may carry a varying degree of organic load in the form of any number of sediments and soluble materials. This water is generally recycled.

Water can also be used in some of processing stages to further clean, cool, heat, cook, or otherwise modify the food in some fashion prior to packaging. Process water as defined above can sometimes be used once and discarded. However, often times a major portion of this process water is re-used and is, therefore, subject to organic and microbial contamination. In some stages this process water stream is also used to transport the food. In other stages, the process water can be a separate stream and is recycled apart from the transport water. In either situation, the process water becomes contaminated with organic matter from the food, providing nutrients for microbial growth in the water.

Given the nature of the food as well as the presence of sediments and soluble materials, the water, flume, and other transport or processing equipment may be subject to the growth of unwanted microorganisms. Water that is untreated and recycled during transport or processing accumulates debris and increased microbial populations. Left untreated, recycled water tends to clean produce early in a shift but contaminates produce later in the shift. In fact, flume water has been identified as a potential source of coliform, *E. coli* and *Salmonella* contamination or cross contamination during cider production. These and other microorganisms are generally undesirable to the food, the water, the flume and can cause buildup on all water contact surfaces of slime or biofilm, which requires frequent cleaning to remove.

Microbial contamination or cross contamination of fruits and vegetables via water continues to be a major concern for produce packers, processors and end users. Although washing fresh produce with water can reduce potential contamination, the wash water can also serve as a source of contamination or cross contamination. If pathogenic microorganisms in water are not removed, inactivated or otherwise controlled, they can spread to surrounding produce, potentially contaminating them. Further, handling or processing steps that pool many individual fruits or vegetables tend to increase the risk that a single contaminated item may contaminate the entire lot. Immersing or spray-washing fruits and vegetables in fresh water can help reduce surface populations of microorganisms. However sterilization by repeated washing, even with sterile water, cannot be achieved because microorganisms within tissues of produce remain in place.

The addition of antimicrobial agents to recycled handling or process water can inactivate most vegetative cells in water, helping avoid cross contamination. Ideally, an antimicrobial agent or compound used in such a system will have several important properties in addition to its antimicrobial efficacy. The compound or agent should have no residual antimicrobial activity on the food. Residual activity implies the presence of a film of antimicrobial material which will continue to have antimicrobial effect which may require further rinsing of the food product. The antimicrobial agent preferably should also be odor free to prevent transfer of undesirable odors onto food stuffs. If direct food contact occurs, the antimicrobial agent should also be composed of food additive materials which will not effect food if contamination occurs, nor affect humans should incidental ingestion result. In addition, the antimicrobial agent should preferably be composed of naturally occurring or innocuous ingredients, which are chemically compatible with the environment and cause no concerns for toxic residues within the water.

In the past, transport and process water apparatus have generally been treated with sodium hypochlorite and chlorine dioxide. Generally, these materials are effective in preventing the unwanted growth of microorganisms. However, the use rate of these chlorine-based antimicrobials is very high because they tend to be rapidly consumed by the high organic load included in both the fruits or vegetables and soil. Further, upon consumption, compounds such as chlorine dioxide decompose producing byproducts such as chlorites and chlorates, while hypochlorite produces trichloromethanes which may be toxic in very low concentrations. Lastly, chlorine dioxide is a toxic gas with an acceptable air concentration limit of 0.1 ppm. Exposure to $ClO_2$ often leads to headaches, nausea, and respiratory problems, requiring expensive and intricate safety devices and equipment when it is used.

Further, the efficacy of these common antimicrobial agents on the surface of fruits and vegetables is often limited. For example, some workers have reported that chlorine dioxide effectively controlled microbial build-up in the cucumber hydrocooling water but had little effect on microorganisms on or in the fruit. Other workers showed that chlorine treatment had little effect on surface microflora of tomatoes and oranges during a packing operation. Another group concluded that commonly used antimicrobial agents have only minor effects and should not be relied upon to eliminate microorganisms from produce. Washing raw produce with chlorinated water is effective in reducing the microbial load, as long as the proper amount of residual chlorine is maintained.

An antimicrobial agent being used more commonly in fresh produce transport or process water is peroxyacetic acid. The EPA approved a peroxyacetic acid-based composition in 1996 for controlling microbial growth and reducing biofilm formation in fruit and vegetable transport or process waters. From a historical perspective, peroxyacetic acid has been used for food contact surface sanitizing, aseptic packaging and medical device cold-sterilization, among other things. In addition to its biocidal properties, the environmentally-friendly decomposition byproducts and good stability in the presence of vegetable debris helped gain acceptance of this technology among fruit and vegetable packers, handlers, and processors.

Nevertheless, there remains a need for improved antimicrobial compositions for treating waters used for transporting or processing fruits or vegetables.

SUMMARY OF THE INVENTION

The present invention relates to compositions including peroxyacetic acid and peroxyoctanoic acid and methods for preventing microbial growth in aqueous streams including the step of applying a composition of the invention to or as the stream. The aqueous stream can be used for transporting or processing a food or plant product.

The compositions and methods of the invention are unexpectedly effective in preventing the growth of unwanted microorganisms in food transport and processing apparatus and on food and plant products. The compositions and methods of the invention provide an antimicrobial agent useful in water for transporting or processing food products which has a high degree of antimicrobial efficacy and which is safely ingestible by humans while imposing no unacceptable environmental incompatibility.

A preferred antimicrobial composition of the present invention includes acetic acid, octanoic acid, peroxyacetic acid, and peroxyoctanoic acid. A preferred composition preferably includes a combination of peroxyacetic acid and peroxyoctanoic acid effective for killing one or more of *Escherichia coli* O157:H7, *Listeria monocytogenes*, *Salmonella javiana*, yeast, and mold. In a preferred embodiment, the concentrate composition is diluted into flume water employed for transporting or processing fruits and/or vegetables.

In one embodiment, an antimicrobial concentrate composition of the present invention includes about 50 to about 60 weight-% acetic acid, about 10 to about 20 weight-% octanoic acid, and about 5 to about 15 weight-% hydrogen peroxide. In another embodiment, the antimicrobial concentrate composition of the present invention includes an equilibrium mixture resulting from a combination of about 50 to about 60 weight-% acetic acid, about 10 to about 20 weight-% octanoic acid, and about 5 to about 15 weight-% hydrogen peroxide. In a third embodiment, the antimicrobial concentrate composition of the present invention includes about 35 to about 45 weight-% acetic acid, about 5 to about 15 weight-% octanoic acid, about 3 to about 8 weight-% hydrogen peroxide, about 8 to about 16 weight-% peroxyacetic acid, and about 1 to about 5 weight-% peroxyoctanoic acid.

In one embodiment, an antimicrobial use composition of the invention includes about 10 to about 150 ppm acetic acid, about 5 to about 40 ppm octanoic acid, about 4 to about 20 ppm hydrogen peroxide, about 5 to about 50 ppm peroxyacetic acid, and about 2 to about 25 ppm peroxyoctanoic acid.

The compositions of the invention can be employed in methods for controlling microbial growth in an aqueous stream used for transporting or processing food products. These methods include treating the aqueous stream with a concentrate composition of the invention or employing a use composition of the invention for the aqueous stream.

The compositions can include peroxyheptanoic and/or peroxynonanoic acid in place of or in addition to peroxyoctanoic acid.

DETAILED DESCRIPTION OF THE INVENTION

Definitions

As used herein, a processed fruit or vegetable refers to a fruit or vegetable that has been cut, chopped, sliced, peeled, ground, milled, irradiated, frozen, cooked (e.g., blanched, pasteurized), or homogenized. As used herein a fruit or vegetable that has been washed, colored, waxed, hydro-cooled, refrigerated, shelled, or had leaves, stems or husks removed is not processed.

As used herein, the phrase "food product" includes any food substance that might require treatment with an antimicrobial agent or composition and that is edible with or without further preparation. Food products include meat, poultry, fruits and vegetables. The term "produce" refers to food products such as fruits and vegetables and plants or plant-derived materials that are typically sold uncooked and, often, unpackaged, and that can sometimes be eaten raw.

As used herein, the phrase "plant product" includes any plant substance or plant-derived substance that might require treatment with an antimicrobial agent or composition. Plant products include seeds, nuts, nut meats, cut flowers, plants or crops grown or stored in a greenhouse, house plants, and the like.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. Whether or not modified by the term "about", the claims include equivalents to the quantities.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

Composition of Carboxylic Acids and Peroxycarboxylic Acids

Among other constituents, the composition of the present invention includes a carboxylic acid. Generally, carboxylic acids have the formula R—COOH wherein the R can represent any number of different groups including aliphatic groups, alicyclic groups, aromatic groups, heterocyclic groups, all of which can be saturated or unsaturated as well as substituted or unsubstituted. Carboxylic acids also occur having one, two, three, or more carboxyl groups.

Peroxycarboxylic (or percarboxylic) acids generally have the formula $R(CO_3H)_n$, where R is an alkyl, arylalkyl, cycloalkyl, aromatic or heterocyclic group, and n is one, two, or three, and named by prefixing the parent acid with peroxy. While peroxycarboxylic acids are not very stable, their stability generally increases with increasing molecular weight. Thermal decomposition of these acids can generally proceed by free radical and nonradical paths, by photodecomposition or radical-induced decomposition, or by the action of metal ions or complexes. Percarboxylic acids can be made by the direct, acid catalyzed equilibrium action of 30-98 wt. % hydrogen peroxide with the carboxylic acid, by autoxidation of aldehydes, or from acid chlorides, and hydrides, or carboxylic anhydrides with hydrogen or sodium peroxide.

Typically the compositions and methods of the present invention include peroxyacetic acid. Peroxyacetic (or peracetic) acid is a peroxy carboxylic acid having the formula: $CH_3COOOH$. Generally, peroxyacetic acid is a liquid having an acrid odor at higher concentrations and is freely soluble in water, alcohol, ether, and sulfuric acid. Peroxyacetic acid can be prepared through any number of methods known to those of skill in the art including preparation from acetaldehyde and oxygen in the presence of cobalt acetate. A solution of peroxyacetic acid can be obtained by combining acetic acid with hydrogen peroxide. A 50% solution of peroxyacetic acid can be obtained by combining acetic anhydride, hydrogen peroxide and sulfuric acid. Other methods of formulation of peroxyacetic acid include those disclosed in U.S. Pat. No. 2,833,813, which is incorporated herein by reference.

Typically the compositions and methods of the present invention include peroxyoctanoic acid, peroxynonanoic acid, or peroxyheptanoic acid, preferably peroxyoctanoic acid. Peroxyoctanoic (or peroctanoic) acid is a peroxycarboxylic acid having the formula, for example, of n-peroxyoctanoic acid: $CH_3(CH_2)_6OOOH$. Peroxyoctanoic acid can be an acid with a straight chain alkyl moiety, an acid with a branched alkyl moiety, or a mixture thereof. Peroxyoctanoic acid can be prepared through any number of methods known to those of skill in the art. A solution of peroxyoctanoic acid can be obtained by combining octanoic acid and hydrogen peroxide.

A preferred antimicrobial composition of the present invention includes acetic acid, octanoic acid, peroxyacetic acid, and peroxyoctanoic acid. Such a composition can also include a chelating agent. A preferred composition preferably includes a combination of peroxyacetic acid and peroxyoctanoic acid effective for killing one or more of *Escherichia coli* O157:H7, *Listeria monocytogenes, Salmonella javiana,* yeast, and mold. For example, the composition can kill such microbes on the surface of a fruit or vegetable, in water used for transport or processing of the fruit or vegetable, and can reduce or prevent transfer of a microbe from one piece of fruit or vegetable to another (cross contamination). The preferred compositions include concentrate compositions and use compositions. Typically, an antimicrobial concentrate composition can be diluted, for example with water, to form an antimicrobial use composition. In a preferred embodiment, the concentrate composition is diluted into flume water employed for transporting or processing processed or non-processed fruits and/or vegetables.

A preferred antimicrobial concentrate composition of the present invention includes about 50 to about 60 weight-% acetic acid, about 10 to about 20 weight-% octanoic acid, about 5 to about 15 weight-% hydrogen peroxide, and about 0.3 to about 1 weight-% chelating agent. Preferably, such an antimicrobial concentrate composition includes about 54 weight-% acetic acid, about 10 weight-% hydrogen peroxide, about 0.6 weight-% chelating agent, and about 14 weight-% octanoic acid. This concentrate composition can be prepared according to the proportions described above. After combining the ingredients in these proportions, certain ingredients, such as the acetic acid, octanoic acid, and hydrogen peroxide, react to form peroxyacetic acid and peroxyoctanoic acid.

By about two weeks after combining, the reaction of these ingredients has approached equilibrium. That is, the relative amounts of one or more of peroxyacetic acid, acetic acid, peroxyoctanoic acid, octanoic acid, and hydrogen peroxide will be roughly constant. The equilibrium amount will be affected by decomposition or other reaction, if any, of any labile species. A preferred antimicrobial concentrate composition of the present invention includes an equilibrium mixture resulting from a combination of about 50 to about 60 weight-% acetic acid, about 10 to about 20 weight-% octanoic acid, about 5 to about 15 weight-% hydrogen peroxide, and about 0.3 to about 1 weight-% chelating agent. A more preferred antimicrobial concentrate composition of the present invention includes an equilibrium mixture resulting from a combination of about 54 weight-% acetic acid, about 14 weight-% octanoic acid, about 10 weight-% hydrogen peroxide, and about 0.6 weight-% chelating agent.

A preferred antimicrobial concentrate composition of the present invention includes about 35 to about 45 weight-% acetic acid, about 5 to about 15 weight-% octanoic acid, about 3 to about 8 weight-% hydrogen peroxide, about 8 to about 16 weight-% peroxyacetic acid, about 1 to about 5 weight-% peroxyoctanoic acid, and about 0.1 to about 2 weight-% chelating agent. Preferably, such an antimicrobial concentrate composition includes about 40 weight-% acetic acid, about 10 weight-% octanoic acid, about 5 weight-% hydrogen peroxide, about 12 weight-% peroxyacetic acid, about 3 weight-% peroxyoctanoic acid, and about 0.6 weight-% chelating agent. These preferred compositions can be produced by mixing the acid and peroxide components at proportions listed in preceding paragraphs and allowing the composition to sit at ambient temperature for a period of approximately two weeks. That is, these preferred compositions can be considered equilibrium compositions.

The compositions of the present invention also include antimicrobial use compositions. Preferred antimicrobial use compositions include about 10 to about 150 ppm acetic acid, about 5 to about 40 ppm octanoic acid, about 4 to about 20 ppm hydrogen peroxide, about 5 to about 50 ppm peroxyacetic acid, about 2 to about 25 ppm peroxyoctanoic acid, and about 0.2 to about 2.5 ppm chelating agent. Preferably, such an antimicrobial use composition about 133 ppm acetic acid, about 33 ppm octanoic acid, about 17 ppm hydrogen peroxide, about 40 ppm peroxyacetic acid, about 33 ppm peroxyoctanoic acid, and about 2 ppm chelating agent. Different dilutions of a concentrate composition can result in different levels of the components of the use composition, generally maintaining the relative proportions. For example, a use composition of the present invention can have concentrations twice, one half, or one quarter those listed above.

The level of reactive species, such as peroxy acids and/or hydrogen peroxide, in a use composition can be affected, typically diminished, by organic matter that is found in or added to the use composition. For example, when the use composition is a flume transporting fruits or vegetables, fruit or vegetable organic matter or accompanying organic matter will consume peroxy acid and peroxide. Thus, the present amounts of ingredients in the use compositions refer to the composition before or early in use, with the understanding that the amounts will diminish as organic matter is added to the use composition.

In each of the compositions described above, the chelating agent is an optional, but preferred, ingredient. Typically the balance of each of the compositions described above is made up primarily or exclusively of a solvent, such as water, e.g. tap or other potable water.

The compositions of the present invention preferably include only ingredients that can be employed in food products or in food transport, handling, or processing, for example, according to government (e.g. FDA or EPA) rules and regulations. In addition, the present compositions are preferably free of a coupling agent. Preferably, the composition is free of any peroxycarboxylic acid or carboxylic acid with 10 or more carbon atoms. Such 10 or more carbon acids can impart undesirable residues (e.g. bad tasting and/or malodorous) to a fruit or vegetable.

As used herein, a composition or combination "consisting essentially" of certain ingredients refers to a composition including those ingredients and lacking any ingredient that materially affects the basic and novel characteristics of the composition or method. The phrase "consisting essentially of" excludes from the claimed compositions and methods: a coupling agent; an ingredient that cannot be employed in food products or in food transport, handling, or processing according to U.S. government rules or regulations; and/or a peroxycarboxylic acid or carboxylic acid with 10 or more carbon atoms; unless such an ingredient is specifically listed after the phrase.

Each of the compositions listed above can be formulated by combining each of the listed ingredients. In addition, certain compositions including both acid and peroxy acid can be formulated by combining the acids and hydrogen peroxide, which forms peroxy acids. Typically, the pH of an equilibrium mixture is about 1, and the pH of a 10% solution of the equilibrium mixture in water is about 2.4.

Hydrogen Peroxide

The antimicrobial composition of the invention typically also include a hydrogen peroxide constituent. Hydrogen peroxide in combination with the percarboxylic acid provides a surprising level of antimicrobial action against microorganisms despite the presence of high loadings of organic sediment. Additionally, hydrogen peroxide can provide an effervescent action which can irrigate any surface to which it is applied. Hydrogen peroxide works with a mechanical flushing action once applied which further cleans the surface of application. An additional advantage of hydrogen peroxide is the food compatibility of this composition upon use and decomposition. For example, combinations of peroxyacetic acid and hydrogen peroxide result in acetic acid, water, and oxygen upon decomposition all of which are food product compatible.

While many oxidizing agents can be used, hydrogen peroxide is generally preferred for a number of reasons. After application of the $H_2O_2$/peroxyacetic acid germicidal agent, the residue left merely includes water and an acidic constituent. Deposition of these products on the surface of an apparatus, such as a flume, will not adversely effect the apparatus, the handling or processing, or the food products transported therein.

Hydrogen peroxide ($H_2O_2$), has a molecular weight of 34.014 and it is a weakly acidic, clear, colorless liquid. The four atoms are covalently bonded in a H—O—O—H structure. Generally, hydrogen peroxide has a melting point of −0.41° C., a boiling point of 150.2° C., a density at 25° C. of 1.4425 grams per cm$^3$, and a viscosity of 1.245 centipoise at 20° C.

Adjuvants

The antimicrobial composition of the invention can also include any number of adjuvants. Specifically, the composition of the invention can include stabilizing agents, wetting agents, as well as pigments or dyes among any number of constituents which can be added to the composition.

Stabilizing agents can be added to the composition of the invention to stabilize the peracid and hydrogen peroxide and prevent the premature oxidation of this constituent within the composition of the invention. Chelating agents or sequestrants generally useful as stabilizing agents in the present compositions include alkyl diamine polyacetic acid-type chelating agents such as EDTA (ethylene diamine tetraacetate tetrasodium salt), acrylic and polyacrylic acid-type stabilizing agents, phosphonic acid, and phosphonate-type chelating agents among others. Preferable sequestrants include phosphonic acids and phosphonate salts including 1-hydroxy ethyldene-1,1-diphosphonic acid ($CH_3C(PO_3H_2)_2OH$), amino [tri(methylene phosphonic acid)] ($[CH_2PO_3H_2]_2$(ethylene diamine[tetra methylene-phosphonic acid)], 2-phosphene butane-1,2,4-tricarboxylic acid, as well as the alkyl metal salts, ammonium salts, or alkyloyl amine salts, such as mono, di, or tetra-ethanolamine salts. The stabilizing agent is used in a concentration ranging from about 0 weight percent to about 20 weight percent of the composition, preferably from about 0.1 weight percent to about 10 weight percent of the composition, and most preferably from about 0.2 weight percent to 5 weight percent of the composition.

Also useful in the composition of the invention are wetting and defoaming agents. Wetting agents function to increase the penetration activity of the antimicrobial composition of the invention. Wetting agents which can be used in the composition of the invention include any of those constituents known within the art to raise the surface activity of the composition of the invention.

Along these lines surfactants, and especially nonionic surfactants, can also be useful in the present invention. Nonionic surfactants which can be useful in the present invention are those which include ethylene oxide moieties, propylene oxide moieties, as well a mixtures thereof, and ethylene oxide-propylene oxide moieties in either heteric or block formation. Additionally useful in the present invention are nonionic surfactants which include an alkyl ethylene oxide compounds, alkyl propylene oxide compounds, as well as mixtures thereof, and alkyl ethylene oxide-propylene oxide compounds where the ethylene oxide propylene oxide moiety is either in heteric or block formation. Further useful in the present invention are nonionic surfactants having any mixture or combination of ethylene oxide-propylene oxide moieties linked to a alkyl chain where the ethylene oxide and propylene oxide moieties can be in any randomized or ordered pattern and of any specific length. Nonionic surfactants useful in the present invention can also include randomized sections of block and heteric ethylene oxide propylene oxide, or ethylene oxide-propylene oxide.

Generally, the concentration of nonionic surfactant used in a composition of the present invention can range from about 0 wt-% to about 5 wt-% of the composition, preferably from about 0 wt-% to about 2 wt-% of the concentrate composition, and most preferably from about 0 wt-% to about 1 wt-% of the composition.

The composition used in the methods of the invention can also contain additional ingredients as necessary to assist in defoaming.

Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof.

Especially preferable, are those antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 5 wt-%, preferably from about 0.01 wt-% to 2 wt-%, and most preferably from about 0.01 wt-% to about 1 wt-%.

The composition of the invention can also contain any number of other constituents as necessitated by the application, which are known to those of skill in the art and which can facilitate the activity of the present invention. Preferably, the compositions of the present invention are free of a coupling agent.

Methods Employing the Compositions of the Invention

The concentrate and use compositions of the present invention can be employed for a variety of antimicrobial purposes, preferably as or for forming water-based systems for processing and/or transporting processed or unprocessed fruits or vegetables. Preferred methods of the present invention include employing a composition of the invention in a recycled water system, such as a washing, transport, or processing flume. The advantageous stability of the present compositions in such methods which include the presence of fruit or vegetable debris makes these compositions competitive with cheaper, less stable, and potentially toxic chlorinated compounds. Preferred methods employing the present compositions include fruit or vegetable flumes. Conventional fruit or vegetable flume methods employ a sodium/calcium hypochlorite antimicrobial, and the present compositions are an advantageous substitute in these methods. Preferred methods of the present invention include agitation of the use composition, particularly as a concentrate is added to water to make a use composition. Preferred methods include recycled water systems that have some agitation.

The present methods require a certain minimal contact time of the composition with a microbe for occurrence of antimicrobial activity. The contact time can vary with the type of fruit or vegetable, quality of the fruit or vegetable, amount of soil on the fruit or vegetable, number of microorganisms on the fruit or vegetable, temperature of the use composition, or the like. Preferably the exposure time is a least about 60 seconds. The amount of reduction of microbial organisms can vary according to the conditions of use such as: concentration of peroxy acid in the use composition, temperature, exposure time, and the fruit or vegetable surface.

Methods of the invention include applying the present compositions to a food product, a plant product, produce, or a plant. For example, a composition of the invention can be applied to a plant in a green house to remove microbes from or to prevent microbes from establishing themselves on the plant. By way of further example, a composition of the invention can be applied to poultry parts during processing and before packaging to reduce the microbial load on the poultry.

The present invention may be better understood with reference to the following examples. These examples are intended to be representative of specific embodiments of the invention, and are not intended as limiting the scope of the invention.

EXAMPLES

Example 1

Formulas for Peroxyacetic/Peroxyoctanoic Acid Mixtures Having Activity Against Microbes Contaminating Fruits and Vegetables A preferred antimicrobial concentrate composition of the invention was formulated as:

| Raw Material | Weight % |
| --- | --- |
| Glacial Acetic Acid | 54 |
| Hydrogen Peroxide, 35% | 30 |
| HEDP, 60% | 1 |
| Octanoic Acid, 95% | 15 |

This concentrate formulation converted to a composition including peroxy acids during storage for two weeks at generally ambient conditions. In this case, the concentrate composition converted to:

| Chemical | Typical Weight Percent of Chemical In Concentrate 2 Weeks Post-Manufacture |
| --- | --- |
| Acetic Acid | 40% |
| Hydrogen Peroxide | 5% |
| HEDP | 0.6% |
| Octanoic Acid | 10% |
| Peroxyacetic Acid | 12% |
| Peroxyoctanoic Acid | 3% |

The remainder of this concentrate composition was water.

The equilibrated concentrate composition was diluted for use to a typical maximum level of peroxyacetic acid of 40 ppm, and an overall formulation of:

| Chemical | Typical Weight ppm of Chemical in Use-Solution 2 Weeks Post-Manufacture |
| --- | --- |
| Acetic Acid | 133 ppm |
| $H_2O_2$ | 17 ppm |
| HEDP | 2 ppm |
| Octanoic Acid | 33 ppm |

-continued

| Chemical | Typical Weight ppm of Chemical in Use-Solution 2 Weeks Post-Manufacture |
|---|---|
| Peroxyacetic Acid | 40 ppm |
| Peroxyoctanoic Acid | 10 ppm |

The remainder of this use composition was water.

Example 2

Antimicrobial Efficacy of a Peroxyacetic/Peroxyoctanoic Acid Mixture Against Microbes Isolated from Fruits or Vegetables This study compared antimicrobial efficacy of a peroxyacetic acid/peroxyoctanoic acid mixture to peroxyacetic acid alone for application in fruit or vegetable transport or process waters. This study measured the antifungal potency of both chemistries in aqueous systems through laboratory rate-of-kill testing employing fungi harvested from fresh produce.

Materials and Methods

Preparation of Fungi for Rate of Kill Testing

Routine transfer to Sabouraud Dextrose agar slants maintained cultures of *Candida parapsilosis* (from blueberry processing water), *Rhodotorula* species (from celery processing water), *Cryptococcus* species (from potato processing water) and *Zygosaccharomyces bailii* (ATCC 60483). Growth was harvested by adding 5 mL of phosphate buffered water to the slant, mixing and then transferring the suspension into 90 mL of phosphate buffered water. The resulting suspension was used for testing.

Routine transfer to Sabouraud Dextrose agar slants maintained cultures of *Aspergillus* species (from onion processing water), *Penicillium* species (from celery processing water) and *Cladosporium* species (from potato processing water). Conidia suspensions of each mold were prepared by subculturing each mold to Sabouraud Dextrose agar plates and incubating until thick aerial mycelia with conidia were evident. Conidia were harvested by adding approximately 10 mL of phosphate buffered water to the plate, scraping the mycelia and collecting the suspension in a flask. The suspension was filtered through sterile gauze to remove large mycelia fragments from the conidia. The resulting suspension was used for testing.

Preparation of Antimicrobial Agents for Rate of Kill Testing

Two antimicrobial agents were used for testing. The first agent contained peroxyacetic acid. The second contained a peroxyacetic acid/peroxyoctanoic acid mixture. Both agents were diluted in sterile deionized water to achieve a total peracid concentration of 80 ppm. The composition of the use-solutions were as follows:

| Chemical | Peroxyacetic Acid Agent | Peroxyacetic/Peroxyoctanoic Acid Agent |
|---|---|---|
| Peroxyacetic Acid | 80 ppm | 64 ppm |
| Octanoic Acid | None | 53 ppm |
| Peroxyoctanoic Acid | None | 16 ppm |

Measuring Rate of Fungus Kill

The rate at which peroxyacetic acid and a peroxyacetic acid/peroxyoctanoic acid mixture killed fungi was measured by inoculating use-solutions of each antimicrobial agent with fungi and then quantifying survivors after various exposure times.

Testing was performed in duplicate. 99 mL of each antimicrobial use-solution was transferred to a 250 mL Erlenmeyer flask and allowed to equilibrate to 25° C. The liquid in the flask was swirled vigorously in a rapid circular motion and 1 mL of a fungus suspension was added. After 30 seconds, 2, 5 or 10 minutes 1 mL quantities of the use-solution were transferred to 9 mL of an inactivating solution including 0.1% sodium thiosulfate. 1 mL quantities of the inactivating solution were pour-plated using Sabouraud Dextrose agar. Serial 100-fold dilutions of the inactivating solution were also plated. Agar plates were incubated for 72 hours at 26° C. before counting survivors. The log reduction of fungi due to the antimicrobial agent was determined by comparing reduction to a water control.

Results

Rate of Fungus Kill

The starting populations of *Candida parapsilosis*, *Rhodotorula* sp., *Cryptococcus* sp. and *Zygosaccharomyces bailii* in suspension were 7.30, 4.88, 8.08 and 5.98 $\text{Log}_{10}$ CFU/mL respectively. *Cryptococcus* sp. was the most susceptible to both peracid agents (Table 1). The osmophilic yeast *Zygosaccharomyces bailii* was the least susceptible. The peroxyacetic acid/peroxyoctanoic acid mixture reduced the number of yeast cells in suspension faster than the peroxyacetic acid agent.

TABLE 1

Average log reduction of yeast by peroxyacetic acid (POAA) and a peroxyacetic/peroxyoctanoic acid (POAA/POOA) mixture.

|  | 30 Seconds | | 2 Minutes | | 5 Minutes | |
|---|---|---|---|---|---|---|
|  | POAA | POAA/POOA | POAA | POAA/POOA | POAA | POAA/POOA |
| *Candida parapsilosis* | 0.34 | 3.49 | 1.49 | 3.46 | 3.42 | 4.12 |
| *Rhodotorula* sp. | >3.88 | >3.88 | >3.88 | >3.88 | >3.88 | >3.88 |
| *Cryptococcus* sp. | >7.08 | >7.08 | >7.08 | >7.08 | >7.08 | >7.08 |
| *Z. bailii* | 0.16 | 0.42 | 0.18 | 4.32 | 0.94 | 4.80 |

The starting populations of *Aspergillus* sp., *Penicillium* sp. and *Cladosporium* sp. were 6.28, 6.45 and 5.18 $\text{Log}_{10}$ CFU/mL respectively. *Cladosporium* sp. was the most susceptible to both peracid agents (Table 2). *Aspergillus* sp. was the least susceptible. The peroxyacetic acid/peroxyoctanoic acid mixture reduced the number of mold conidia in suspension faster than the peroxyacetic acid agent.

TABLE 2

Average log reduction of mold by peroxyacetic acid (POAA) and a peroxyacetic/peroxyoctanoic acid (POAA/POOA) mixture.

|  | 2 Minutes | | 5 Minutes | | 10 Minutes | |
|---|---|---|---|---|---|---|
|  | POAA | POAA/POOA | POAA | POAA/POOA | POAA | POAA/POOA |
| *Aspergillus* sp. | 0 | 0.13 | 0 | 1.60 | 0 | 2.13 |
| *Penicillium* sp. | 0 | 4.19 | 0.45 | 4.79 | 1.52 | 5.45 |
| *Cladosporium* sp. | 1.86 | >4.18 | 4.18 | >4.18 | >4.18 | >4.18 |

These results can also be expressed as improvements in the kill rate (Table 3). A peroxyacetic/peroxyoctanoic acid mixture typically demonstrates greater kill rate against bacteria, yeast & mold than peroxyacetic acid when diluted to the same concentration of peracid. Improvements in the kill rate are illustrated in Table 3. Kill rate of spoilage yeast and mold kill in suspension is substantially improved:

TABLE 3

Improvement in spoilage fungi kill rate by a peroxyacetic/peroxyoctanoic acid mixture of the present invention.

| Fungus | Improvement in Reduction[a] | | | |
|---|---|---|---|---|
| | 30 sec. | 2 min. | 5 min. | 10 min. |
| Candida parapsilosis (yeast) | +3.15 Log | +1.97 Log | +0.70 Log | — |
| Zygosaccharomyces bailii (yeast) | +0.26 Log | +4.14 Log | +3.86 Log | — |
| Aspergillus sp. (mold) | — | +0.13 Log | +1.60 Log | +2.13 Log |
| Penicillium sp. (mold) | — | +4.19 Log | +4.34 Log | +3.93 Log |
| Fusarium sp. (mold) | — | — | +3.04 Log | +2.30 Log |
| Cladosporium sp. (mold) | — | +2.32 Log | 0 Log | 0 Log |

[a]Improvement in Reduction = (POAA/POOA Log(reduction) − POAA Log (reduction))

Discussion

The predominant microorganisms on fruits or vegetables are mesophilic and psychrotrophic gram-negative bacteria, most commonly *Pseudomonas, Enterobacter* and *Erwinia* species. Coliform bacteria, lactic acid bacteria and fungi typically make up the balance of the total microbe population. During transport or processing, these microorganisms end-up in the recycled wash water and can multiply and grow to high numbers if left unchecked. Because of this, antimicrobial agents used in fruit or vegetable transport or process water should at a minimum control the proliferation of gram-negative bacteria. Without this control, transport or process water quickly becomes a vector for cross-contamination. The more that organisms are reduced the better the preventive action.

Peroxyacetic acid has a history of potency against vegetative bacteria. It provided consistent control of these organisms in this study, including coliform bacteria. The peroxyacetic/peroxyoctanoic acid mixture showed greater antibacterial activity than peroxyacetic acid by itself against bacteria at the same total peracid concentration. Another of the peroxyacetic/peroxyoctanoic acid mixture's strengths appears to be as a broader spectrum and more potent fungicide than peroxyacetic acid.

Conclusions

Testing in laboratory aqueous systems indicated that the peroxyacetic/peroxyoctanoic acid mixture had broader spectrum, more potent antifungal efficacy than peroxyacetic acid. The peroxyacetic/peroxyoctanoic acid mixture provided a better antimicrobial efficacy profile for treatment of fruit or vegetable transport or process water.

Example 3

Antimicrobial Efficacy of a Peroxyacetic/Peroxyoctanoic Acid Mixture in Fruit or Vegetable Transport and Process Waters This study compared antimicrobial efficacy of a peroxyacetic acid/peroxyoctanoic acid mixture to peroxyacetic acid alone for application in fruit or vegetable transport and process waters. This study was performed during actual vegetable processing served to evaluate microbial counts in wash water and on fresh-cut vegetables exposed to peracid-treated waters.

Materials and Methods

Concentration of Antimicrobial Agents in Fresh-Cut Vegetable Processing Water

Vegetable processing water testing was done using the same antimicrobial agents as in laboratory aqueous system testing. The varying concentrations of each agent are listed in the results section. Municipal tap water was the diluent.

Antimicrobial Efficacy in Vegetable Processing Water

The reduction of microorganisms in vegetable processing water treated with peroxyacetic acid or a peroxyacetic acid/peroxyoctanoic acid mixture was determined. Testing was done in two separate recycled water systems. In both systems, cut vegetables fell into a water stream that carried them to a de-watering area where they were collected for further processing. The water that the vegetables traveled in was routed to a balance tank that fed back into the original water stream thus completing the process loop. One system was used to wash cut, raw celery or cabbage. The other system was used to transport cut, raw potatoes to a blancher.

During processing of each vegetable, 10 water samples were collected in sterile plastic bags containing an inactivating agent (0.01% sodium thiosulfate). 1 mL quantities were plated on Petrifilm® (3M, Inc.) Aerobic Plate Count, Coliform Count and Yeast & Mold Count media. Validation of these media using this procedure was performed prior to initiating testing (data not presented). Serial 100-fold dilutions were also plated. Petrifilms were incubated at 35° C. for 24 hours (Coliform Count), 35° C. for 48 hours (Aerobic Plate Count), or at room temperature for 72 hours (Yeast & Mold Count). The number of microorganisms was counted following incubation.

Antimicrobial Efficacy on Fresh-Cut Vegetables

Microorganism reduction on vegetable surfaces in the transport and process water was determined while water analyses were being conducted. Ten samples of each cut vegetable were collected just prior to falling into the process water stream and just after de-watering.

Eleven grams of each sample were transferred to bag containing 99 mL of sterile phosphate buffered water. Contents of the bag were mixed in a Stomacher brand mixer for approximately 1 minute. Afterwards, 1 mL of the mixture was plated on Petrifilm brand Aerobic Plate Count, Coliform Count and Yeast & Mold Count media. 1 mL quantities of 100-fold serial dilutions were also plated. Petrifilms were incubated and enumerated as described above in this Example.

Statistical Analyses

A single-factor analysis of variance (ANOVA) using Microsoft Excel software was used to determine if microorganism numbers in transport and process water treated with the peroxyacetic acid/peroxyoctanoic mixture were significantly lower than those with peroxyacetic acid. At an alpha level of 0.05, if results showed that $P \leq 0.05$, a significant lowering was concluded. The same analysis was used to evaluate the significance of reduction on vegetable surfaces.

Results

Antimicrobial Efficacy in Fresh-Cut Vegetable Processing Water

The concentration of total peracid in the celery and cabbage processing water was approximately the same for both chemicals. The concentration of total peracid from the peroxyacetic acid agent in the potato process water was approximately 20 ppm greater than the total peracid concentration from the peroxyacetic/peroxyoctanoic acid mixture. Both the peroxyacetic and peroxyacetic/peroxyoctanoic acid mixture reduced the number of coliform bacteria to levels undetected by the test protocol (Table 4). The celery process water treated with the peroxyacetic/peroxyoctanoic acid mixture showed significantly lower numbers of total aerobic bacteria than peroxyacetic acid treated water ($P \leq 0.05$). No significant difference in total bacteria numbers was observed in cabbage or potato water. All process waters treated with the peroxyacetic/peroxyoctanoic acid mixture showed significantly lower numbers of yeast and mold than peroxyacetic acid treated water ($P \leq 0.05$).

TABLE 4

Average number (log CFU/mL) of microorganisms in fresh-cut vegetable process water containing peroxyacetic acid (POAA) or a peroxyacetic/peroxyoctanoic acid (POAA/POOA) mixture.

| | Aerobic Plate Count | | Coliform Count | | Yeast & Mold Count | |
|---|---|---|---|---|---|---|
| | POAA | POAA/POOA | POAA | POAA/POOA | POAA | POAA/POOA |
| Celery[a] | 2.02 | 1.21 | 0 | 0 | 1.86 | 0.32 |
| Cabbage[b] | 1.92 | 1.78 | 0 | 0 | 2.02 | 0.97 |
| Potatoes[c] | 0.92 | 0.95 | 0 | 0 | 5.48 | 2.67 |

[a]Average concentration of peracid from POAA agent = 38 ppm, from POAA/POOA agent = 39 ppm.
[b]Average concentration of peracid from POAA agent = 26 ppm, from POAA/POOA agent = 29 ppm.
[c]Average concentration of peracid from POAA agent = 54 ppm, from POAA/POOA agent = 32 ppm.

Antimicrobial Efficacy on Fresh-Cut Vegetables

The peroxyacetic/peroxyoctanoic acid mixture showed significantly greater reductions of coliform bacteria on celery and yeast and mold on potatoes than peroxyacetic acid ($P \leq 0.05$) (Table 5).

TABLE 5

Average log reduction of microorganisms on fresh-cut vegetables after 30 second exposure to process water containing peroxyacetic acid (POAA) or a peroxyacetic/peroxyoctanoic acid (POAA/POOA) mixture.

| | Aerobic Bacteria Reduction | | Coliform Bacteria Reduction | | Yeast & Mold Reduction | |
|---|---|---|---|---|---|---|
| | POAA | POAA/POOA | POAA | POAA/POOA | POAA | POAA/POOA |
| Celery[a] | 1.07 | 1.09 | 0.77 | 1.41 | 0.68 | 0.96 |
| Cabbage[b] | 0.84 | 0.85 | >0.88 | >0.23 | 0.77 | 0.82 |
| Potatoes[c] | 1.54 | 1.59 | >1.58 | >1.66 | No reduction, count increase of 2.87 | No reduction, count increase of 0.83 |

[a]Average concentration of peracid from POAA agent = 38 ppm, from POAA/POOA agent = 39 ppm.
[b]Average concentration of peracid from POAA agent = 26 ppm, from POAA/POOA agent = 29 ppm.
[c]Average concentration of peracid from POAA agent = 54 ppm, from POAA/POOA agent = 32 ppm.

Discussion

The predominant microorganisms on fresh-cut fruits or vegetables and in the water used to wash them are mesophilic and psychrotrophic gram-negative bacteria, most commonly *Pseudomonas, Enterobacter* and *Erwinia* species. Coliform bacteria, lactic acid bacteria and fungi typically make up the balance of the total microbial population. During transport or processing, these microorganisms end-up in the recycled wash water and can multiply and grow to high numbers if left unchecked. Because of this, antimicrobial agents used in fruit or vegetable transport or process water should at a minimum control the proliferation of gram-negative bacteria. Without this control, transport or process water quickly becomes a vector for cross-contamination. The more that organisms are reduced the better the preventive action.

Peroxyacetic acid has a history of potency against vegetative bacteria. It provided consistent control of these organisms in this study, including coliform bacteria. The peroxyacetic/peroxyoctanoic acid mixture showed greater antibacterial activity than peroxyacetic acid by itself against bacteria at the same total peracid concentration. However, one of the peroxyacetic/peroxyoctanoic acid mixture's strengths appears to be as a broader spectrum and more potent fungicide than peroxyacetic acid. It substantially reduced yeast and mold numbers in transport and process water, which led to less fungus cross-contamination depositing on fresh-cut fruit or vegetable surfaces.

Conclusions

Under actual processing conditions, the peroxyacetic/peroxyoctanoic acid mixture showed greater antibacterial activity than peroxyacetic acid. It also substantially reduced yeast and mold numbers in transport and process water, leading to less fungus cross-contamination depositing on fresh-cut fruit or vegetable surfaces. The peroxyacetic/peroxyoctanoic acid mixture provided a better antimicrobial efficacy profile for treatment of fresh-cut fruit or vegetable process water.

Example 4

Peroxyacetic/Peroxyoctanoic Acid Mixtures Exhibit Superior Activity Against Pathogenic Bacteria Historical data on chlorine and sodium/calcium hypochlorite indicates that these chemicals have antimicrobial properties. Because of these properties, they are used in fruit and vegetable transport or process water to reduce microbial contamination. Unlike chlorinated competitors, the present peroxyacetic/peroxyoctanoic acid mixtures offer advantageous antimicrobial efficacy against pathogenic bacteria.

Materials and Methods

The following procedure was employed for determining whether a composition killed pathogenic bacteria (e.g. *Escherichia coli* O157:H7, *Listeria monocytogenes*, or *Salmonella javiana*) on the surface of a fruit or vegetable. Bacteria were applied to tomato surfaces and allowed a 1-2 hour attachment time. Contaminated tomatoes were submersed in a peroxyacetic/peroxyoctanoic acid mixture according to the present invention (at a level yielding 40 ppm peroxyacetic acid) or water for 1 minute without agitation. After 1 minute, tomatoes were transferred to a solution that neutralized the peroxy acids and peroxides and massaged for 3 minutes to remove attached bacteria. The number of attached bacteria that survived treatment was determined using standard agar plating technique. The number of bacteria that "fell off" the tomato into the water or peroxyacetic/peroxyoctanoic acid mixture according to the present invention, and survived, was also determined by neutralization and agar plating technique. A similar experiment was conducted employing a peroxyacetic acid antimicrobial composition.

The following procedure was employed for testing the ability of a composition to reduce the number of pathogenic bacteria (e.g. *Escherichia coli* O157:H7, *Listeria monocytogenes,* or *Salmonella javiana*) on the surface of fruits and vegetables that occurred through cross-contamination. Bacteria were applied to cherry tomato surfaces and allowed a 24-hour attachment time. The inoculated tomatoes, along with some non-inoculated tomatoes, were submersed in a peroxyacetic/peroxyoctanoic acid mixture according to the present invention (at a level yielding 40 ppm peroxyacetic acid) or water for 1 minute with agitation. After 1 minute, non-inoculated tomatoes were removed and transferred to a solution that neutralized the peroxy acids and peroxides. The neutralizing solution was vortex mixed for 45 seconds to remove cross-contaminated bacteria. The number of cross-contaminated bacteria that survived treatment was determined using standard agar plating technique.

Results

Figure 1:
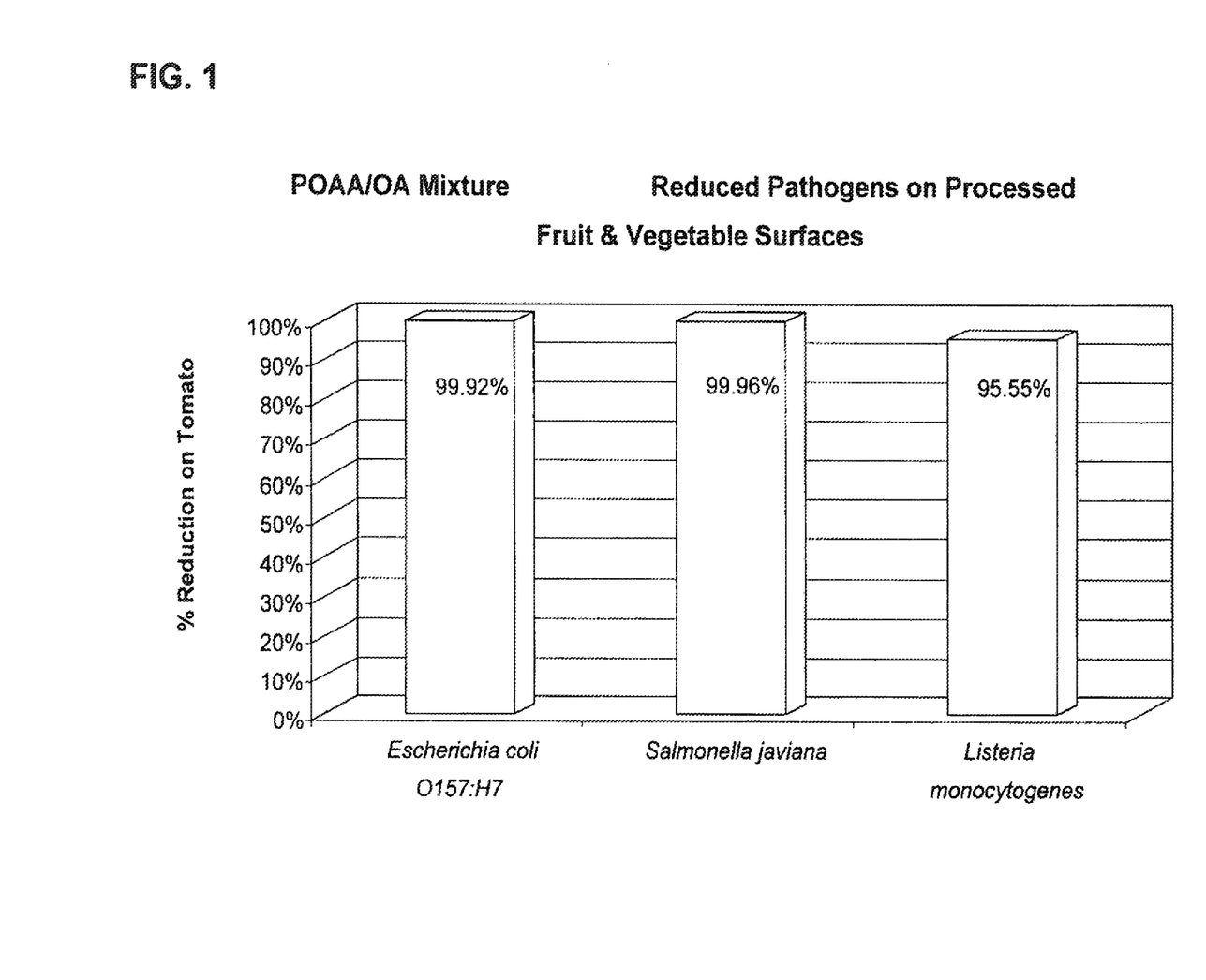
FIG. 1 illustrates reduction of pathogens on the surface of fruits and vegetables by a peroxyacetic acid/peroxyoctanoic acid mixture of the present invention.
Figure 2:
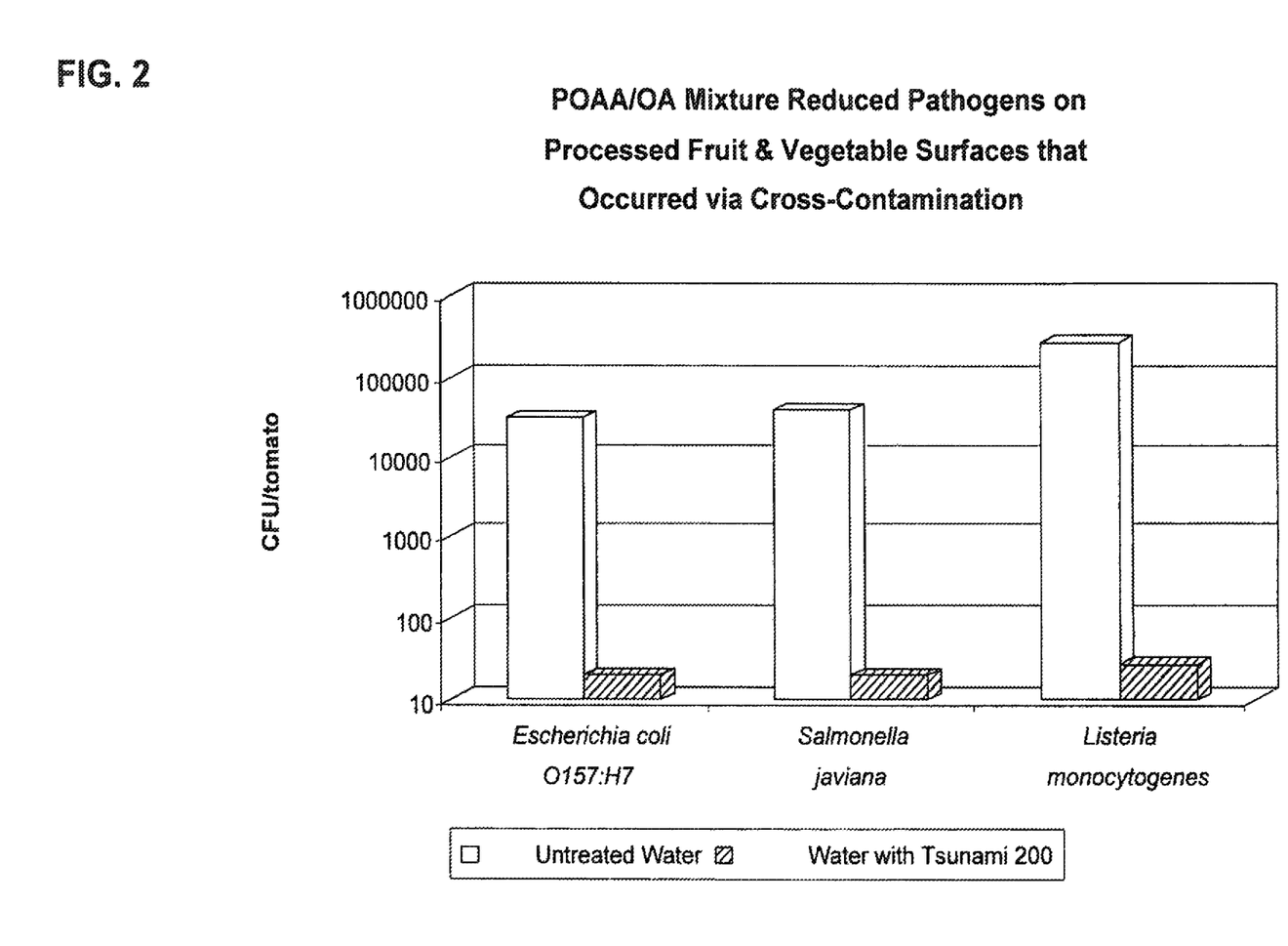
FIG. 2 illustrates reduced cross contamination by pathogens when fruit or vegetable handling water includes a peroxyacetic acid/peroxyoctanoic acid mixture of the present invention.

A peroxyacetic/peroxyoctanoic acid mixture according to the present invention significantly lowered the numbers of all three bacteria on tomato surfaces (FIG. 1). It also reduced the numbers all three bacteria suspended in solution by >99% compared to water. This mixture also significantly lowered the number of cross-contaminated bacteria on tomato surfaces compared to water (FIG. 2).

A peroxyacetic acid composition (lacking peroxyoctanoic acid) caused reductions in pathogenic bacteria that were smaller than those achieved with the peroxyacetic/peroxyoctanoic acid mixture. For example, 20 ppm POAA produced only a 57% reduction in the *E. coli* O157:H7 in tomato wash water; at 40 ppm the reduction was 88%, and at 60 ppm the reduction was 94%. For *L. monocytogenes* on tomatoes, POAA produced a reduction of 84% at 20 ppm, of 95% at 40 ppm, and of 98% at 60 ppm. At 20 and 40 ppm, POAA produced no reduction in amounts of *S. javiana*, but at 60 ppm the reduction was 91%.

Discussion

It is possible to reduce the numbers of pathogenic bacteria on produce surfaces through cleansing action alone, for example, submersing broccoli in a soap-based solution. The problem with this reduction method is that bacteria removed from the surface may remain viable and transfer to other food or equipment surfaces. This transfer of bacteria is known as cross-contamination. Fortunately, mixtures of the present invention reduced the numbers of *Escherichia coli* O157:H7, *Listeria monocytogenes,* and *Salmonella javiana* on fruit and vegetable surfaces that occurred through cross-contamination. These reductions were superior to those produced by much larger amounts of peroxyacetic acid.

Conclusions

The compositions of the present invention reduced the numbers of *Escherichia coli* O157:H7, *Listeria monocytogenes* and *Salmonella javiana* on fruit and vegetable surfaces through bactericidal activity, and also reduced cross-contamination. Reducing through bactericidal/killing activity versus physical removal is one advantage of the present compositions.

Example 5

A Peroxyacetic/Peroxyoctanoic Acid Mixture Has No Adverse Effect on Appearance of Fruits or Vegetables Certain antimicrobial agents, such as high levels of chlorine, can have adverse effects on the appearance of fresh cut fruits or vegetables. This example demonstrates that a peroxyacetic/peroxyoctanoic acid mixture of the present invention has no adverse effect on the appearance of fresh-cut fruits or vegetables.

Materials and Methods

The effect of a peroxyacetic/peroxyoctanoic acid mixture of the present invention on vegetable appearance was studied. Processed vegetables were exposed to water, chlorinated water, and water containing a peroxyacetic/peroxyoctanoic acid mixture of the present invention, which had the same formula as the mixtures employed in Examples 2 and 3. Vegetables were then spun to remove excess moisture, packaged in sealed plastic bags and refrigerated. Appearance was noted daily for 1 week and the results are reported in Table 6, below.

Results

Processed vegetables treated with water containing a peroxyacetic/peroxyoctanoic acid mixture of the present invention did not appear any different than those treated with water or a low level of chlorine (Table 6).

TABLE 6

Appearance of refrigerated processed vegetables over 1 week after a 10 minute submersion in water, sodium hypochlorite or a peroxyacetic/peroxyoctanoic acid mixture of the present invention.

| | Vegetable Appearance Over 1 Week at 40° F. | |
| --- | --- | --- |
| Vegetable | Sodium Hypochlorite (40 ppm available chlorine, pH 6.5) | Peroxyacetic/Peroxyoctanoic Acid mixture (40 ppm peroxyacetic acid) |
| Chopped Lettuce | Same as water treated | Same as water treated |
| Shredded Carrots | Same as water treated | Same as water treated |
| Chopped Onions | Same as water treated | Same as water treated |
| Chopped Celery | Same as water treated | Same as water treated |
| Diced Tomatoes | Same as water treated | Same as water treated |
| Sliced Potatoes | Same as water treated | Same as water treated |
| Cut Green Beans | Same as water treated | Same as water treated |
| Chopped Cabbage | Same as water treated | Same as water treated |
| Cut Sweet Corn | Same as water treated | Same as water treated |

Discussion

Appearance changes are the result of spoilage mechanisms. Spoilage development usually coincides with growth of microorganisms, but this does not necessarily mean that all spoilage is of microbial origin. In fact, the events that usually begin spoilage in a processing environment are physical damage and normal enzymatic reactions. Microbial degradation usually occurs as a result of these two events. Chlorine is still used as an antimicrobial agent in wash water for produce. High dosages (200-300 ppm) are often used to meet the chlorine demand of large wash systems. It is believed that such high chlorine levels can cause adverse discoloration and leave off-flavors in fresh processed produce.

Conclusions

Accelerated spoilage is usually the result of physical injury and enzymatic oxidation that leads to microbial degradation—not poor microorganism removal during washing. The high levels of chlorine sometimes needed for washing can cause discoloration or off-flavors on processed fruits or vegetables. Processed fruits or vegetables treated with water containing a peroxyacetic/peroxyoctanoic acid mixture of the present invention did not appear any different than those treated with water or low levels of chlorine.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. An antimicrobial use composition comprising:
    a food product and about 10 to about 150 ppm acetic acid, about 5 to about 40 ppm octanoic acid, about 4 to about 20 ppm hydrogen peroxide, about 5 to about 50 ppm peroxyacetic acid, about 2 to about 25 ppm peroxyoctanoic acid, and about 0.2 to about 2.5 ppm chelating agent
    wherein the composition comprises at least 1 part by weight of peroxyoctanoic acid for each about 5 parts of peroxyacetic acid.

2. The antimicrobial use composition of claim 1, comprising the food product, about 133 ppm acetic acid, about 33 ppm octanoic acid, about 17 ppm hydrogen peroxide, about 40 ppm peroxyacetic acid, about 25 ppm peroxyoctanoic acid, and about 2 ppm chelating agent.

3. The antimicrobial use composition of claim 1, wherein the composition is free of carboxylic acids with 10 or more carbon atoms and peroxycarboxylic acids with 10 or more carbon atoms.

4. A method of controlling microbial growth in an aqueous stream used for transporting or processing food product, the method comprising:
    applying an antimicrobial concentrate composition comprising acetic acid, octanoic acid, hydrogen peroxide, peroxyacetic acid, peroxyoctanoic acid, and chelating agent and a food product to the aqueous stream to produce the antimicrobial use composition of claim 1.

5. A method of preparing an antimicrobial use composition comprising:
    1) diluting an antimicrobial concentrate composition comprising about 35 to about 45 weight-% acetic acid, about 5 to about 15 weight-% octanoic acid, about 3 to about 8weight-% hydrogen peroxide, about 8-16 weight-% peroxyacetic acid, about 1-5 weight-% peroxyoctanoic acid, and about 0.1 to about 2 weight-% chelating agent with water to form a diluted solution, and
    2) applying the diluted solution to a food product to produce the antimicrobial use composition comprising the food product and about 10 to about 150 ppm acetic acid, about 5 to about 40 ppm octanoic acid, about 4 to about 20 ppm hydrogen peroxide, about 5 to about 50 ppm peroxyacetic acid, about 2 to about 25 ppm peroxyoctanoic acid, and about 0.2 to about 2.5 ppm chelating agent, wherein the composition comprises at least 1 part by weight of peroxyoctanoic acid for each about 5 parts of peroxyacetic acid.

6. The method of preparing an antimicrobial use composition of claim 5, wherein the antimicrobial concentrate composition is prepared by mixing 50-60 weight-% acetic acid, about 10 -20 weight-% octanoic acid, about 5-15 weight-% hydrogen peroxide, and about 0.3-1 weight-% chelating agent in water and allowing the composition to equilibrate.

7. A method of controlling microbial growth in an aqueous stream used for transporting or processing food product, the method comprising:
    1) administering an antimicrobial concentrate composition to the stream, the antimicrobial concentrate composition comprising an equilibrium mixture resulting from a composition of about 35 to about 45 weight-% acetic acid, about 5 to about 15 weight-% octanoic acid, about 3 to about 8 weight-% hydrogen peroxide, about 8-16 weight-% peroxyacetic acid, about 1-5 weight-% peroxyoctanoic acid, and about 0.1 to about 2weight-% chelating agent, wherein administering the antimicrobial concentrate composition to the stream produces an antimicrobial use composition comprising:
    about 10 to about 150 ppm acetic acid, about 5 to about 40 ppm octanoic acid,
    about 4 to about 20 ppm hydrogen peroxide, about 5 to about 50 ppm peroxyacetic acid, about 2 to about 25 ppm peroxyoctanoic acid, and about 0.2 to about 2.5 ppm chelating agent,
    wherein the use composition comprises at least 1 part by weight of peroxyoctanoic acid for each about 5 parts of peroxyacetic acid; and
    2) using the aqueous stream comprising the antimicrobial use composition to transport or process the food product.

* * * * *